United States Patent [19]
Robertson

[11] Patent Number: 5,836,920
[45] Date of Patent: Nov. 17, 1998

[54] NEEDLE GUARD

[76] Inventor: William Frost Robertson, The Hollins, 103 Smithy Bridge Road, Littleborough Lancashire OL15 0BQ, United Kingdom

[21] Appl. No.: 809,218
[22] PCT Filed: Sep. 20, 1995
[86] PCT No.: PCT/GB95/02256
  § 371 Date: Mar. 18, 1997
  § 102(e) Date: Mar. 18, 1997
[87] PCT Pub. No.: WO96/09083
  PCT Pub. Date: Mar. 28, 1996

[30] Foreign Application Priority Data

Sep. 24, 1994 [GB] United Kingdom .................... 9419316

[51] Int. Cl.$^6$ ..................................................... A61M 5/32
[52] U.S. Cl. ........................................... 604/192; 604/263
[58] Field of Search .................................... 604/192, 110, 604/198, 263, 187

[56] References Cited

U.S. PATENT DOCUMENTS

| 4,867,746 | 9/1989 | Dufresne | 604/192 |
| 5,092,461 | 3/1992 | Adam | 604/263 X |
| 5,135,509 | 8/1992 | Olliffe | 604/192 |
| 5,256,152 | 10/1993 | Marks | 604/192 X |

FOREIGN PATENT DOCUMENTS

| 0343438 | 11/1989 | European Pat. Off. . |
| 0460914 | 12/1991 | European Pat. Off. . |
| 9318809 | 9/1993 | WIPO . |

*Primary Examiner*—John D. Yasko
*Attorney, Agent, or Firm*—Harrison & Egbert

[57] ABSTRACT

A guard for a hypodermic needle that includes a hub for attachment to a needle and a shield which can be attached to the hub. The shield is adapted to lie adjacent the needle and has a lip which projects outwardly to cover the tip of the needle. An enclosure for the tip of the needle is provided and located adjacent to the lip. The hub and the shield each includes complementary attachment mechanisms whereby the shield can be attached to the hub in first and second relative positions. In the first position, the needle can be used and the shield is capable of moving away from the needle to uncover the tip as the needle initially penetrates the body of a patient and of returning back toward the needle and again to cover the tip as the needle is withdrawn from the patient. By pulling the shield toward the hub in a direction substantially parallel to the longitudinal axis of the needle, the shield is attached to the hub in a second relative position wherein the tip of the needle is enclosed by the enclosure and thereby locks the shield in position with respect to the needle so that the shield cannot be flexed away from the needle to uncover the tip after use.

9 Claims, 6 Drawing Sheets

FIG. 13 ary, the sheath and the needle base comprise 
NEEDLE GUARD

TECHNICAL FIELD

The present invention relates to a guard for a hypodermic needle and needle cannula for use in the prevention of accidental needle-stick injuries.

BACKGROUND ART

To protect medical personnel from accidental needle-stick injuries, several different types of needle assemblies have been proposed for use with syringes and cannulas. In some of these, a syringe needle is automatically withdrawn into the barrel of the syringe on release of the syringe plunger. In others, a sleeve covering the barrel can be moved to cover the needle after an injection has taken place. Sometimes, the needle assembly is provided with a protective cap which can be moved from a position adjacent the needle tip to one over the needle point after use. Such an assembly is described in European Patent Application EP-A-0460914 wherein an elongate protective sheath is located around a needle and is pivotally mounted to a base from which the needle protrudes. The sheath defines an elongate opening through which the needle can pass as the sheath is pivoted away or towards the needle, for example before or after use respectively. In addition, the sheath and the needle base comprise complementary holding means whereby the sleeve is displaceable in a longitudinal direction to locate the needle tip in a sleeved portion of the sheath, thus preventing the needle from being pivotted out of the sheath via the slot.

However, this and the other aforementioned conventional arrangements suffer from at least one of two serious disadvantages: they are either expensive to manufacture, or they are not fail safe as they require the person using the needle to take some positive action to cover the needle tip after use.

It will be appreciated that these disadvantages are serious because unless a needle guard is inexpensive relative to the cost of the needle assembly being used it will tend not to be used as a matter of routine. Similarly, devices which require action by medical staff to make them safe do not give adequate protection against accidental injuries caused, for example if the needle is dropped after use or if the patient is difficult to handle. In addition, sometimes the very act of making the needle safe can force the user to come close to touching the tip of the needle.

In European Patent Application EP-A-0 343 438 is disclosed a needle shield which comprises a flexible elongated device which extends over and along a needle top and both sides thereof with a hood shield at one end for extending over the point of the needle. In use, when a user wishes to insert the needle through a patient's skin, the blunt hood shield at the front end is pressed against the skin of the patient and the needle inserted. Immediately after removal of the needle from the patient's skin, the shield moves automatically back into place over the point of the needle. In a modification, a frictional locking arrangement can be provided which the user may utilize for holding the shield firmly in place over the needle when it is not being used either before or after contamination.

Such a needle shield as described in this European specification is an improvement over the other devices previously mentioned because the shield moves automatically back into place after use. However, it does have several disadvantages. First, despite the fact that a locking arrangement can be provided to hold the hood of the shield in place over the needle tip, even when locked in position there is nothing to stop the shield from being flexed back adjacent the locking arrangement to expose the needle tip. Second, when the locking arrangement is provided it inhibits automatic coverage of the needle tip by the hood shield after use of the needle. Third, the needle tip in this arrangement is never enclosed either before or after needle use and whilst the hood shield provides protection against needle stick injury if a user moves directly longitudinally with respect to the needle, injuries caused by grazing or side-swipe are still possible.

In WO93/18809 is disclosed a needle guard which comprises a shield with a lip, which projects outwardly from the shield so as to cover the tip of the needle when the needle is not in use, and a locking arrangement which can be used to lock the shield in position with respect to the needle after use. Here, the locking arrangement defines a receptacle capable of enclosing the tip of the needle so that the shield cannot be flexed away from the needle to uncover the tip. However, the receptacle is only accessible via a keyhole through which the tip of the needle must be maneuvered by the application of pressure to the guard. In order to apply pressure to the guard, after withdrawal of the needle from a patient, the needle arrangement and guard must be turned over and pressed against a hard surface in order to force the tip of the needle through the keyhole. Thus, the success of the locking arrangement is dependent on the viability of the needle and whether a hard surface is close by. In addition, the manufacture of such a guard is relatively expensive.

The object of the present invention is to provide a device for use in the prevention of needle-stick injuries which obviates or substantially mitigates the afore-mentioned disadvantages of conventional arrangements.

SUMMARY OF THE INVENTION

According to the present invention there is provided a guard for a needle comprising a hub for attachment to a needle cannula, a shield which can be attached to the hub and which is adapted to lie adjacent the needle, a lip which projects outwardly from the shield so as to cover the tip of the needle, and an enclosure means for the tip of the needle located adjacent the lip, and characterized in that the hub and the shield each comprise complementary attachment means whereby the shield can be attached to the hub in a first relative position wherein the needle can be used and the shield is capable of flexing away from the needle to uncover the tip as the lip is pressed against the body of a patient and the needle initially penetrates the body and of resiling automatically back towards the needle as the needle is withdrawn from the patient so that the lip again covers the tip, and whereby by pulling the shield towards the hub in a direction substantially parallel to the longitudinal axis of the needle, the shield is attached to the hub in a second relative position thereto wherein the tip of the needle is enclosed by the enclosure means and thereby locks the shield in position with respect to the needle so that the shield cannot be flexed away from the needle to uncover the tip after use.

Preferably, the complementary attachment means comprise snap-fit fasteners.

Preferably also, the snap-fit fasteners comprise at least one projection and two longitudinally adjacent complementarily shaped grooves into which the projection can fit, location of the projection in a first of the grooves providing attachment of the shield to the hub in the first relative position, and the pulling of the shield towards the hub in a direction substantially parallel to the longitudinal axis of the needle disengaging the projection from the first groove and engaging it in the second groove to provide attachment of the shield. to the hub in the second relative position, the second groove being of greater depth than the first groove so that after engagement the projection cannot be disengaged therefrom manually.

Preferably also, the projection has a ratchet tooth cross-section and the complementarily shaped grooves comprise substantially V-shaped notches.

DETAILED DESCRIPTION OF THE INVENTION

The needle guard of the invention comprises a hub 1 and a shield 2 incorporating a protective, projecting lip 3 at one end. Preferably, the hub 1 and the shield 2 each comprise one-piece plastics mouldings but they could be made in any manner either in one piece or in parts from suitable materials.

Figure 3:
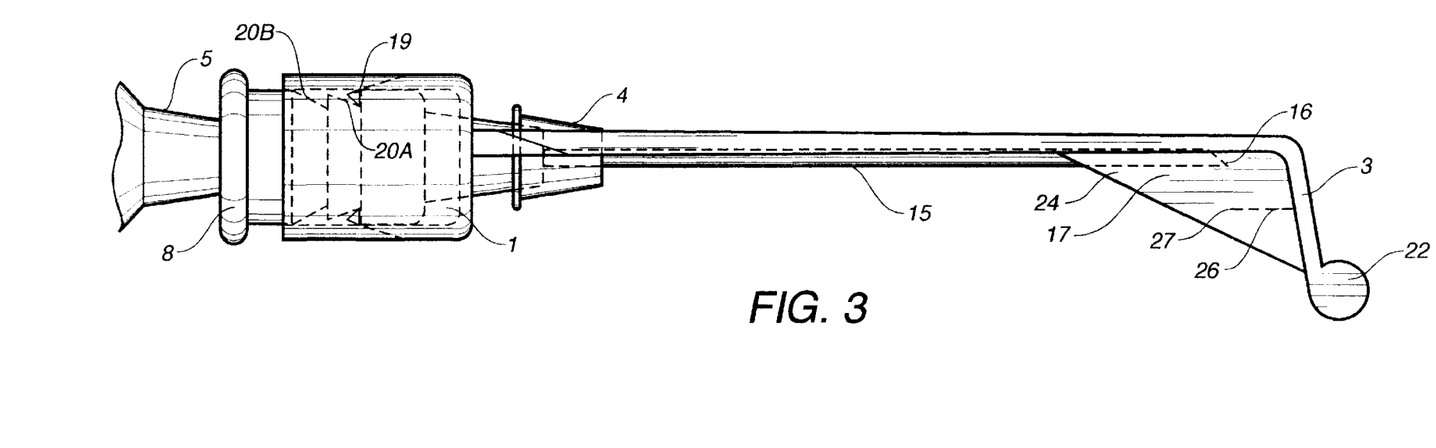
FIG. 3 is a view similar to FIG. 2 showing the guard after attachment to a needle carrier in a position ready for insertion of the needle into a patient.
Figure 4:
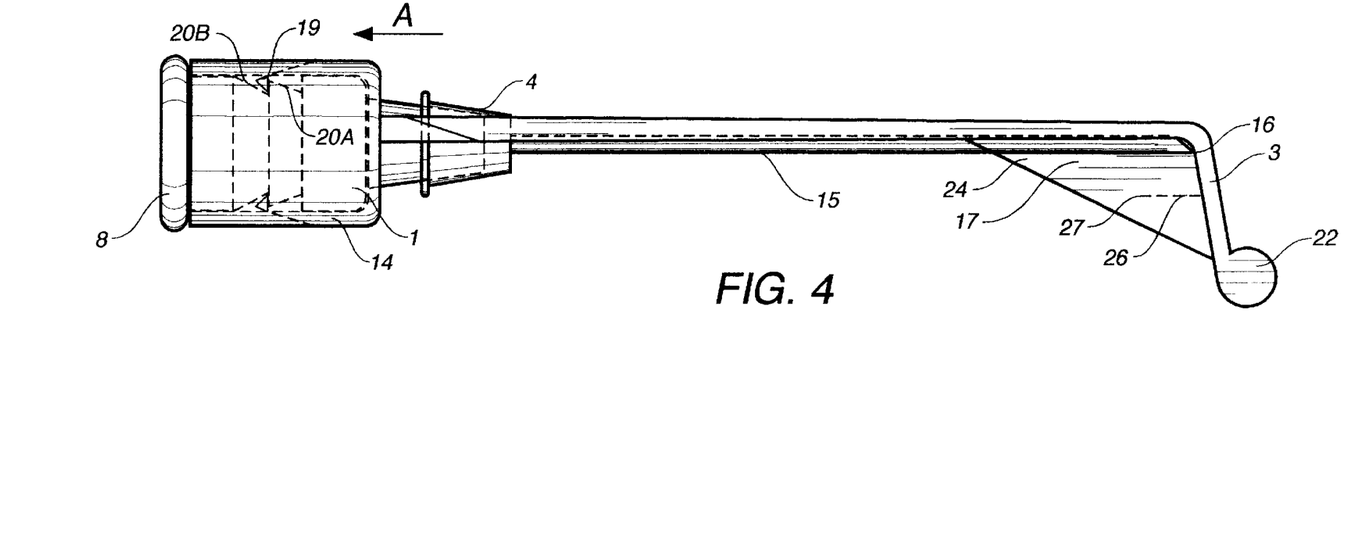
FIG. 4 is a view similar to FIG. 3 showing the hub and the shield in a second relative position wherein the shield has been locked to the needle.
Figure 6:
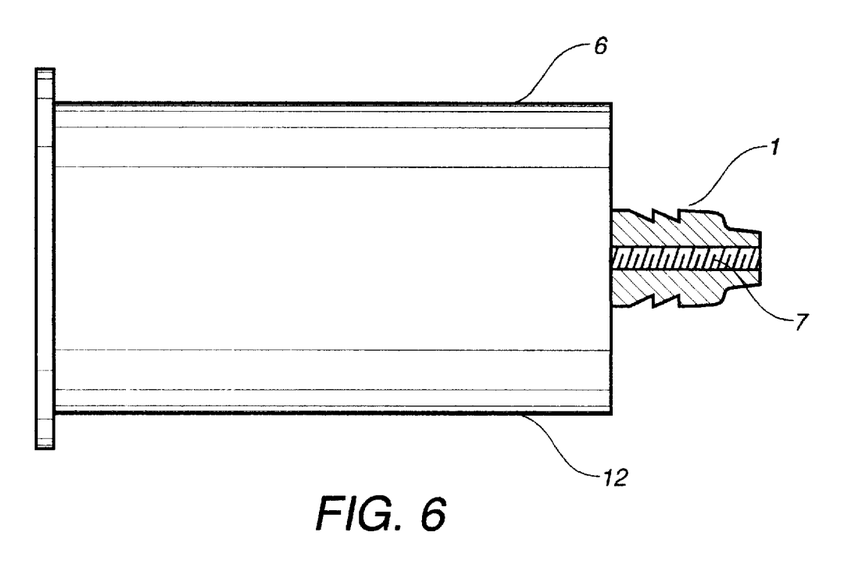
FIG. 6 is a side view of an evacuated blood collection holder with a needle connector modified to form part of the needle guard according to the invention.
Figure 7:
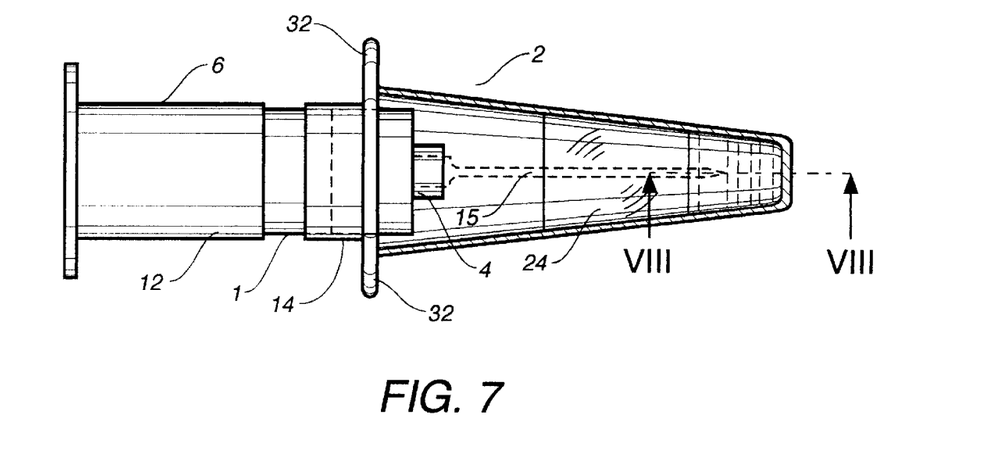
FIG. 7 is a plan view of a second embodiment of an evacuated blood collection holder modified to form part of a second embodiment of needle guard.

The hub 1 can either be made so that it can be located between and attached to a conventional needle hub 4 and an associated assembly 5 such as a syringe body, as shown in FIGS. 3 and 4, or made an integral part of such a needle assembly 6, as shown in FIGS. 6 and 7.

Figures 1A, 1B:
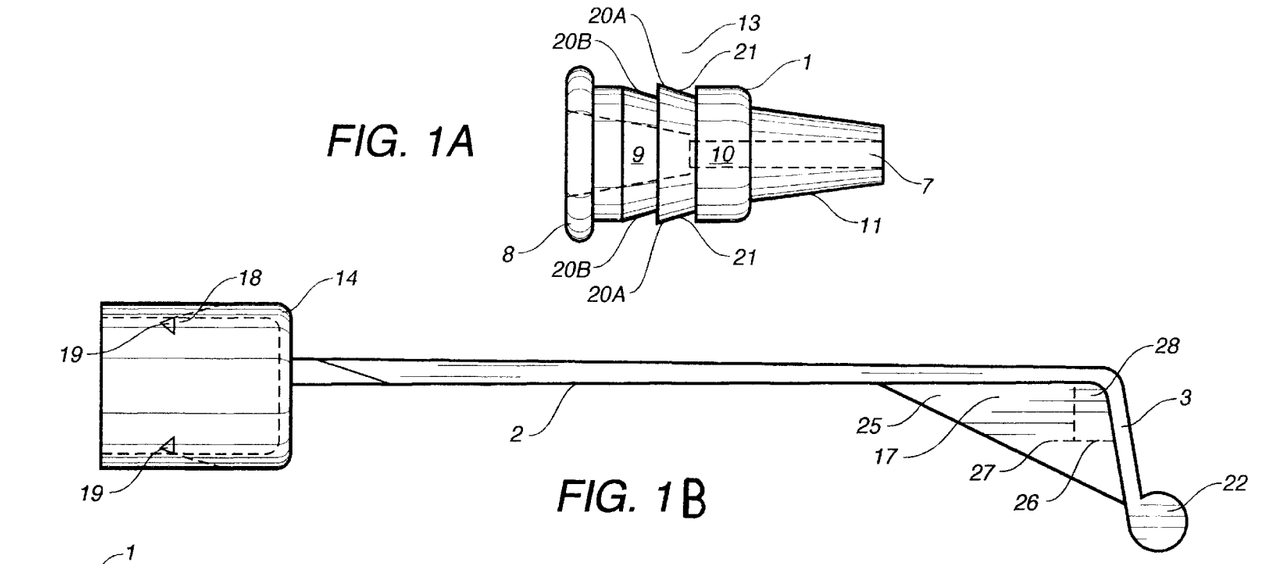
FIGS. 1a and 1b respectively are side views of a hub and a shield forming part of a needle guard according to the invention and prior to attachment to one another.
Figure 2:
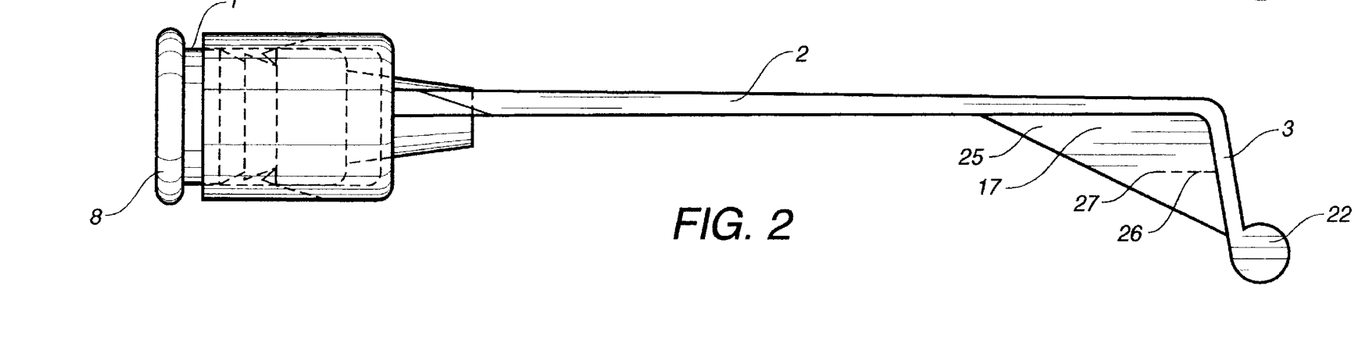
FIG. 2 is a side view of the hub and the shield shown in FIG. 1 when attached to one another in a first relative position.

In the former case, as shown in FIG. 1, the hub 1 comprises a cylindrical plug with a longitudinal passageway 7 therethrough and an enlarged rounded rim 8. The rim 8 provides a gripper to enable connection of the hub 1 to the assembly 5. At its end adjacent the rim 8, the central passageway 7 is shaped to form a female luer slip 9 for attachment to the assembly 5. At the other end of the hub 1, the passageway 7 is shaped into a cylindrical tube 10 within an external male luer slip 11 for connection to the needle hub 4.

However, in the latter case, as shown in FIG. 6, the female luer slip 9 is omitted and the hub 1 is simply formed with an appropriately shaped central passageway 7 for connection with the interior of a barrel 12 of the assembly 6 at one end and the central tube through a needle hub 4 at the other end.

Alternatively, the barrel 12 itself of the assembly 6 can be adapted to form the hub 1, as shown in FIG. 7.

Although not shown in the drawings, it will be appreciated that it is also possible for the hub 1 to be formed integrally with a needle cannula, dispensing with the need for the male luer slip 11.

In all cases, the exterior surface of the hub 1 is provided with an attachment means 13 comprising part of a snap-fit fastener by means of which the hub 1 can be attached to the shield 2.

As shown in FIGS. 1 to 7, the shield 2 comprises one or more elongate arms which are attached to a ring 14 at the end opposite the lip 3. In use, the body of the shield 2 lies adjacent to and parallel to the longitudinal axis of a needle 15 attached to the needle hub 4. The shield 2 is longer than the needle 15 and the lip 3 projects outwardly of the shield 2 and transversely with respect to the needle 15, so as to cover the needle tip 16. As is described in greater detail below, the lip 3 also defines an enclosure means 17 which can enclose the tip 16 of the needle 15 after use.

The shield 2 can be formed with one arm, either running alongside the needle or curved around it; or be a part circular strip from hub 1 to lip 3; or, as in the present examples, any combination of one or two parallel arms with a curvature before the lip 3 to allow maximum view of the needle tip 16 and its entry site.

The ring 14 is intended to fit over the hub 1 and is provided with an attachment means 18 which is of a complementary shape to that of the attachment means 13 formed on the hub 1 and comprises the counterpart of the snap-fit fastener.

The attachment means 13 and 18 comprise respectively at least one projection 19 and first and second longitudinally adjacent complementarily shaped grooves 20A and 20B into which the projection 19 can fit. Although it will be appreciated that the projection 19 could be formed on the hub 1 and the grooves 20A, 20B within the ring 14. Preferably, as shown in FIG. 1 to 6, the projection 19 comprises an opposed pair of ratchet teeth and the grooves 20 comprise substantially V-shaped notches or circular grooves. Alternatively, the teeth can be replaced by an annular projection as is the case in FIG. 7.

The annular nature of the projection 19 in FIG. 7 has the advantage in this case that the shield 2 can be rotated with respect to the hub 1. In an evacuated blood collection holder as shown in FIG. 7, the needle 15 is screwed to the needle hub 4 of the assembly immediately prior to use. The shield 2 can then be rotated so that it is presented correctly with respect to the chamfered tip 16 of the needle 15 for use.

The grooves 20A and 20B and the surface profile 21 of the hub 1 therebetween are fashioned so that the first groove 20A closest to the male luer slip 11 or needle hub 4 is more shallow than the second groove 20B which is closer to the rim 8.

The location of the teeth 19 in the first groove 20A attaches the shield 2 to the hub 1 in a first relative position wherein the shield 2 will protect against needle-stick injuries prior to and immediately after use of the needle assembly. However, relative movement of the shield 2 and the hub 1, achieved in practice by pulling the shield 2 towards the hub 1 in a direction A (see FIG. 4) substantially parallel to the longitudinal axis of the needle 15, disengages the teeth 19 from the first groove 20A and engages them in the second groove 20B to provide attachment of the shield to the hub in a second relative position, wherein the shield 2 is locked to the needle 15. It will be appreciated that the greater depth of the second groove 20B ensures that after engagement the teeth 19 cannot be disengaged from the groove 20B manually and the shield 2 is irreversibly attached to the hub 1. In order to prevent inadvertant locking when the shield 2 is being attached to the hub 1 in its first relative position, the surface profile 21 is inclined so that a greater degree of force is required to move the shield 2 in the direction A into its second relative position than to attach it to the hub 1 initially.

Preferably, the shape of the teeth 19, the groove 20A and. the surrounding surface profile of the hub 1 is such that even after attachment of the shield 2 to the hub 1 in the first relative position, the shield 2 cannot be disengaged from the hub 1 manually by pulling of the shield 2 away from the hub 1 in a direction towards the tip 16 of the needle 15.

The end of the shield 2 adjacent the lip 3 will now be described in greater detail. Here, the projecting edge of the lip 3 is preferably formed with a rounded surface as it will rest and rub against the skin of a patient during use of the needle 4. This can be accomplished, as shown in the drawings, by the provision of an enlarged cylindrical rim 22. Alternatively, the lip 3 can be formed by a U-shaped bend in the end portion of the shield 2. Both of these arrangements have the advantage that the lip 3 is thereby made sufficiently resilient to absorb the impact of the needle 4 if the needle assembly is dropped on its end.

Figure 5:
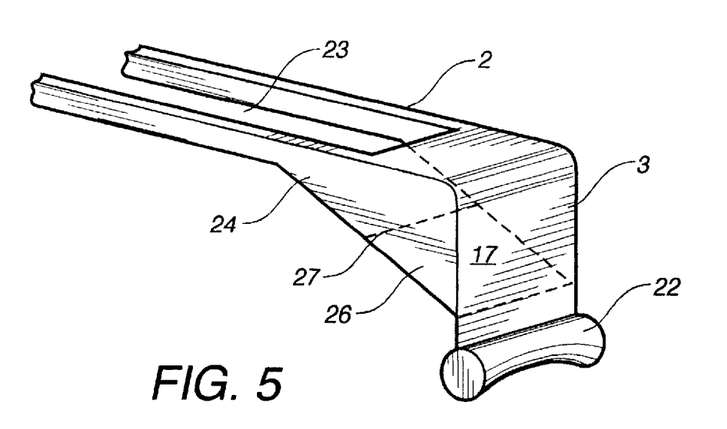
FIG. 5 is a perspective view of one end of a modified shield.

Preferably, the rim 22 is centrally indented or waisted, as shown in FIG. 5, so that in use on withdrawal of the needle 4 from a patient, the rim 22 does not touch the cannulation site. This prevents the rim 22 both from being contaminated by and from contaminating the patient.

Between the hub 1 and the lip 3, the central portion of the shield 2 defines an aperture 23 through which the stem of the needle 15 and, in use, its tip 16 can be seen. In a modification as shown in FIG. 7, a magnifying lens 24 can be located in the aperture 23 above the needle tip 16 to assist in placement of the needle tip 16 during use.

At each side of the shield 2 projecting between the lip 3 and a central portion of the shield 2 is a strengthening web 25. The webs 25 also assist in retention of the tip 16 of the needle 15 prior to use so that it remains covered by the lip 3 when not in use, particularly if it is dropped or mishandled.

In a first embodiment as shown in FIG. 5, the lip 3 and the adjacent portions of the body of the shield 2 and the strengthening webs 25 comprise four sides of a box-like receptacle which comprises the enclosure means. The box shape is completed by a fifth side formed by a web 26. The web 26 is attached to the lip 3 and stretches between the webs.25. The web 26 can lie parallel to the body of the shield as shown in FIGS. 1 to 4 but it is preferably angled away from the needle 15 and connected to the webs 25 along their edges as shown in FIG. 5. When the hub 1 and the shield 2 are in their first relative position, the free edge 27 of the web 26 adjacent the tip 16 of the needle 15 is spaced very slightly from the tip 16 so that the shield 2 can lift away from the needle 15. However, the body of the shield 2 opposite the web 26 which forms the opposed side of the box overlaps the tip 16 of the needle 15 very slightly. In this way, under normal circumstances the shield 2 always remains on one side of the needle 15 with lip 3 covering the needle tip 16.

However, when the shield 2 and the hub 1 are placed in their second relative position, the tip 16 of the needle 15 is forced into the open-sided box 17 and enclosed by it. The shield 2 is thereby locked to the needle 15 so that it cannot be flexed away from the needle 15 to uncover the tip 16. In addition, the way in which the web 26 is angled away from the needle increases the probability that any fluids which escape from the needle tip 16 after enclosure in the receptacle 17 are retained therein. Such fluids can also be trapped within the receptacle 17 by including within the receptacle a pad 28 of an absorbent material, as shown in FIG. 1b, into which the tip 16 of the needle 15 penetrates as it enters the receptacle 17.

Figure 8:
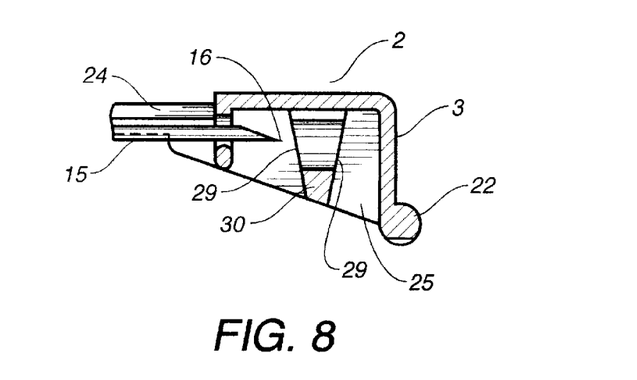
FIG. 8 is a section along the line VIII—VIII in FIG. 7.

In a second arrangement as shown in FIG. 8. embodiment, the enclosure means 17 comprises at least one, but preferably at least two, membranes 29 which extend between the webs 25 from the shield 2 to a retaining bar 30 fastened to the webs 25. When the shield 2 is moved into its second position relative to the hub 1 to secure the needle 15, the needle tip 16 pushes through these membranes 29 which thereby plug the lumen of the needle 15 to prevent fluid loss. Alternatively (not shown), the enclosure means 17 may comprise a block of rigid yet penetrable material secured to the lip 3 and into which the tip 16 of the needle 15 is inserted when the hub 1 and the shield 2 are manipulated into their second relative position.

Figure 9:
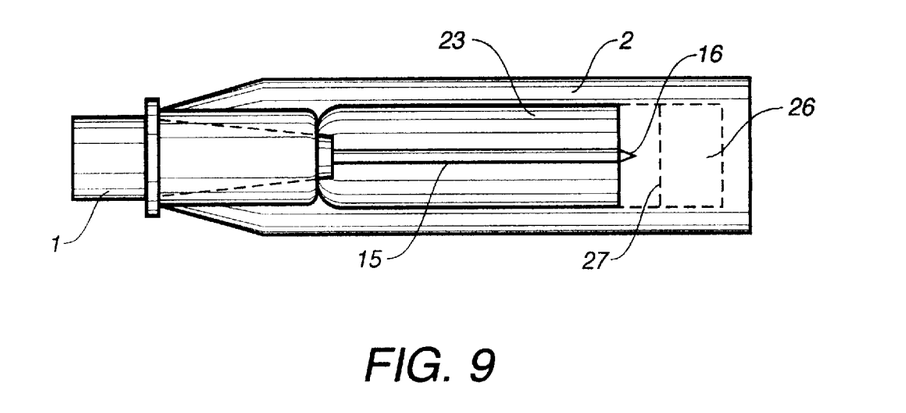
FIGS. 9 to 12 are a sequence of plan, underside and two side schematic views respectively of a needle assembly comprising a guard according to the invention in a sequence prior to and during its use.
Figure 10:
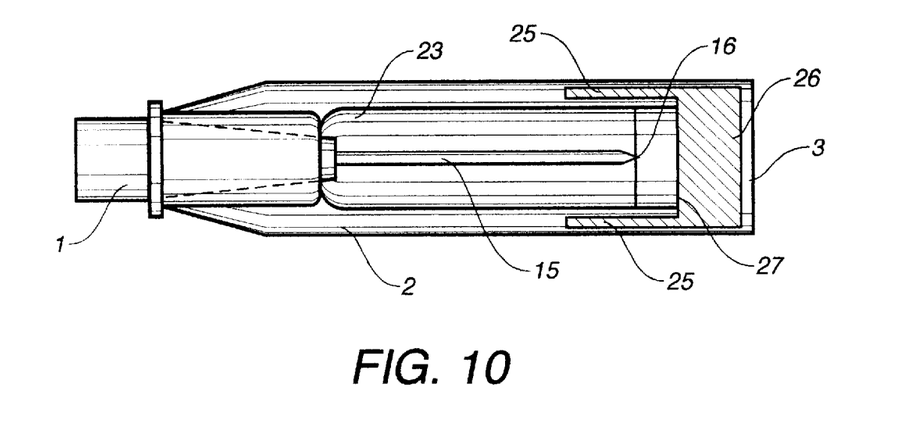
Figure 11:
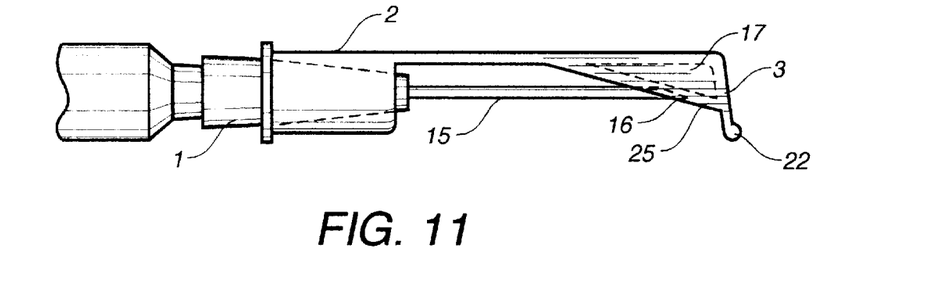
Figure 12:
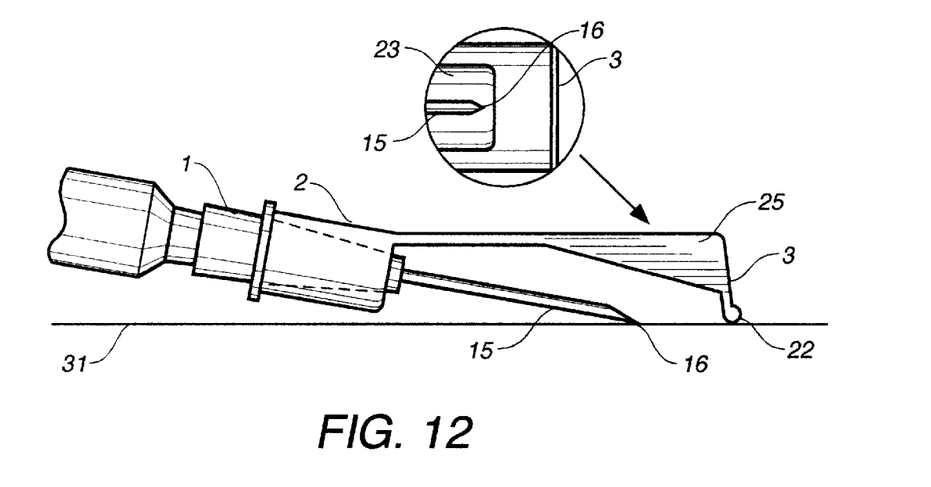

As shown in the sequence of drawings comprising FIGS. 9 to 13, prior to use as shown in FIGS. 9, 10 and 11 the needle 15 lies centrally of the shield 2 adjacent the enclosure means 17 with the lip 3 covering the needle tip 16. When in use at the point of cannulation, as shown in FIG. 12, the needle assembly is positioned so that the shield 2 lies above the needle 15 with the rounded surface 22 of the lip 3 resting on the surface of the patient's skin 31. The tip 16 and the intended site of its entry into the patient can be seen through the aperture 23 or the magnifying glass 24 and the needle assembly can then be employed in the usual way. As the needle 15 penetrates the patient, the shield 2 lifts away from the needle 15 and rides along the skin surface. However, as the shield 2 is resilient, when the needle 15 is withdrawn, it returns back towards the needle 15 until finally, as the tip 16 is withdrawn, the lip 3 immediately covers it.

Figure 13:
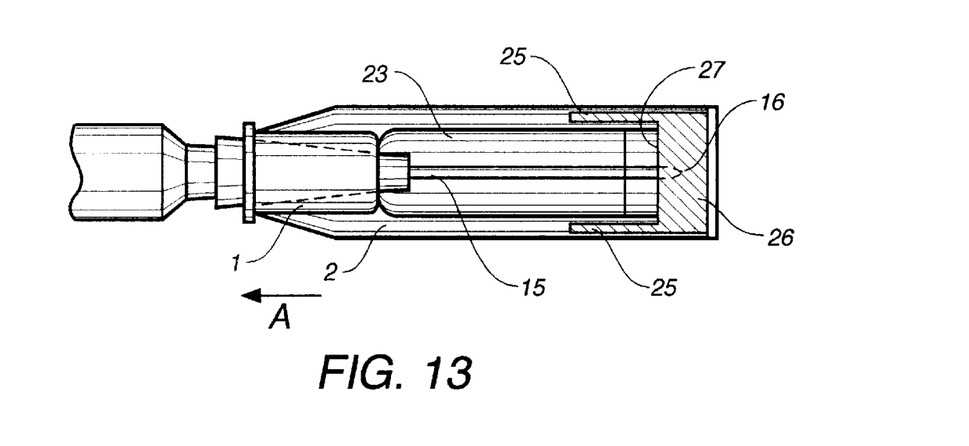
FIG. 13 is an underside schematic view of the needle assembly shown in FIGS. 9 to 12 after use with the shield locked to the needle.

The used needle 15 can now be locked to the shield 2, as shown in FIG. 13, as previously described by pulling the shield 2 towards the hub 1 in a direction substantially parallel to the longitudinal axis of the needle 15. This action disengages the teeth 19 from the first groove 20A and engages them in the deeper second groove 20B from which they cannot be disengaged manually. In this position, the shield 2 cannot be accidentally bent away from the needle 15 to expose the tip 16. However, even in an unlocked state, if the assembly is accidentally dropped, the shield 2 will remain adjacent the needle 15 with the lip 3 covering the tip 16 to prevent needle-stick injuries.

To assist the user in the locking operation, finger pulls 32, as shown in FIG. 7, can be provided projecting laterally on each side of the shield 2. Alternatively, the finger pulls 32 could be extended to form a complete annular collar.

In the foregoing examples, the shield 2 is made of a resilient material which causes the shield to lift away from the needle 15 during use to permit cannulation and return back into position thereafter. However, the shield 2 could be made of a rigid material and the ring 14 hinged to the rest of the shield 2 by any suitable hinge arrangement which is biased so as to ensure the shield 2 returns back to a position adjacent the needle 15 after being move away therefrom. A conventional spring-loaded hinge could be used or alternatively the main body of the shield 2 could be attached to the ring 14 by a strip of resilient material which will flex.

It will be appreciated that the needle guard according to the invention is suitable for use with all needle and cannula assemblies and is not dependent on the size of needle or its function, being suitable for vena puncture, subcutaneous and subcuticular injections as well as cannulation. For example, it can be used as part of a butterfly needle set.

The size, weight and flexibility of the guard can be adapted as required without compromising its effectiveness or significantly affecting its cost. In addition, the guard is compact, is inexpensive to produce and requires no assembly other than fitment to a needle carrier or needle assembly if not integrally formed therewith.

I claim:

1. A guard for a needle cannula comprising:

a hub means for attachment to a needle;

a shield which can be attached to the hub means and which is adapted to lie adjacent the needle;

a lip which projects outwardly from the shield so as to cover the tip of the needle; and an enclosure means for the tip of the needle located adjacent the lip, the hub means and the shield each comprise complementary attachment means whereby the shield can be attached to the hub means in a first relative position wherein the needle can be used and the shield is capable of flexing away from the needle to uncover the tip as the lip is pressed against the body of a patient and the needle initially penetrates the body and of returning automatically back towards the needle as the needle is withdrawn from the patient so that the lip again covers the tip, and whereby by pulling the shield towards the hub means in a direction substantially parallel to the longitudinal axis of the needle, the shield is attached to the hub means in a second relative position thereto wherein the tip of the needle is enclosed by the enclosure means and thereby locks the shield in position with respect to the needle so that the shield cannot be flexed away from the needle to uncover the tip after use, said complementary attachment means comprise snap-fit fasteners said snap-fit fasteners comprise at least one projection and two longitudinally adjacent complementarily shaped grooves into which the projection can fit, a location of the projection in a first of the grooves providing attachment of the shield to the hub means in the first relative position, and the pulling of the shield towards the hub means in a direction substantially parallel to the longitudinal axis of the needle disengaging the projection from the first groove and engaging it in the second groove to provide attachment of the shield to the hub means in the second relative position, the second groove being of greater depth than the first groove so that after engagement the projection cannot be disengaged therefrom manually.

2. The guard as claimed in claim 1, wherein the projection has a ratchet tooth cross-section and the complementarily shaped grooves comprise substantially V-shaped notches.

3. The guard as claimed in claim 1, wherein the enclosure means comprises an open-ended box-like receptacle which is integrally formed with the lip and projects towards the needle.

4. The guard as claimed in claim 3, wherein opposed side walls of the box-like receptacle comprise strengthening webs which extend between the lip and the shield.

5. The guard as claimed in claim 1, wherein prior to use the tip of the needle can rest on one side of the box-like receptacle, the opposite side of the box being of a lesser depth to enable the shield to move laterally away from the needle when in use.

6. The guard as claimed in claim 1, wherein the enclosure means comprises an absorbent pad into which the tip of the needle penetrates as the shield is pulled towards the hub to lock the shield to the hub means.

7. The guard as claimed in claim 1, wherein the lip is provided with a rounded surface to facilitate its travel along the skin of the patient.

8. The guard as claimed in claim 1, wherein the lip is indented to prevent it from touching the cannulation site.

9. The guard as claimed in claim 1, wherein the shield defines an aperture between the hub means and the lip to permit the tip of the needle to be seen as the shield moves away from the needle immediately prior to use.

* * * * *